United States Patent [19]

Stephenson

[11] Patent Number: 4,773,532

[45] Date of Patent: Sep. 27, 1988

[54] DISPENSING SYSTEM FOR STERILE GLOVES

[76] Inventor: Mark Stephenson, 709 Goldsboro Ave., Virginia Beach, Va. 23451

[21] Appl. No.: 172,489

[22] Filed: Mar. 24, 1988

[51] Int. Cl.$^4$ .............................................. B65D 85/66
[52] U.S. Cl. .................................. 206/278; 206/438; 206/390
[58] Field of Search .............. 206/438, 286, 278, 299, 206/484, 390; 223/111

[56] References Cited

U.S. PATENT DOCUMENTS

| | | | |
|---|---|---|---|
| 3,372,799 | 3/1968 | Abildgaard | 206/278 |
| 3,870,150 | 3/1975 | Hummel | 206/278 |
| 4,034,853 | 7/1977 | Smith | 206/278 |
| 4,099,614 | 7/1978 | Heissenberger | 206/438 |
| 4,155,494 | 5/1979 | Poncy et al. | 206/438 |
| 4,677,697 | 7/1987 | Hayes | 206/278 |

Primary Examiner—Joseph Man-Fu Moy
Attorney, Agent, or Firm—Norman B. Rainer

[57] ABSTRACT

A package of a multitude of flattened sterile surgical gloves is provided in roll form. The roll is a continuous spirally wound impervious backing sheet having uniformly spaced parallel transverse tear lines. The gloves are attached by adhesive to the sheet between the tear lines, the cuff portions being upwardly directed. Structure is associated with the cuff portion to cause the glove to automatically open at the cuff, thereby facilitating insertion of a hand into the glove.

8 Claims, 2 Drawing Sheets

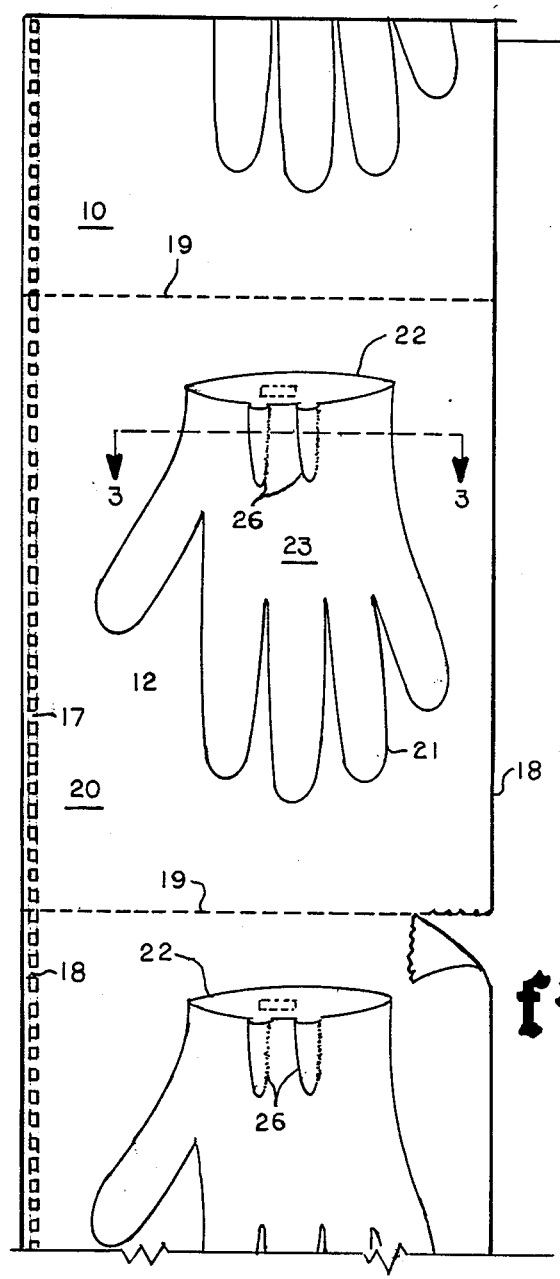
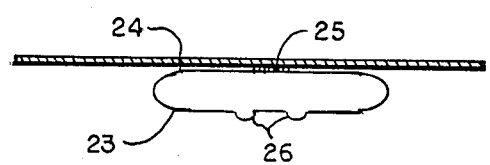
fig. 2
fig. 3

DISPENSING SYSTEM FOR STERILE GLOVES

BACKGROUND OF THE INVENTION

This invention concerns gloves, and more particularly relates to a system for packaging and dispensing sterile surgical gloves.

Surgical gloves, because of their resilient, form-fitting nature, are not easily emplaced upon the hand without assistance from others. When packaging sterilized pairs of gloves intended for use in medical or dental procedures, several factors must be taken into account. Firstly, the package should be of a nature such as to prevent contamination of the gloves during storage and handling. Secondly, the gloves should be disposed in a manner facilitating their removal from the package without difficulty and placed upon the hands of the surgeon or the like without contamination. Thirdly, the package should be amenable to automated production to achieve acceptably low costs.

Packaging methods for sterile surgical gloves have been earlier disclosed, such as in U.S. Pat. Nos. 3,372,799; 4,099,614; and 4,155,494. Packaging techniques for inexpensive gloves formed by the heat bonding of two layers of polyethylene have been disclosed in U.S. Pat. Nos. 3,870,150; 4,034,853; and 4,677,697, said techniques generally involving the disposition of a multitude of the gloves sequentially in a roll configuration.

The aforesaid earlier techniques for packaging surgical sterile gloves leave much to be desired in terms of the ease with which the gloves are properly deployed from their packaged state, and the cost of such techniques. The known methods for packaging polyethylene gloves, although providing minimal cost, are not conducive to the packaging of sterile latex-type surgical gloves because of the difficulty in deploying the gloves from the package under sterile conditions.

It is accordingly a primary object of the present invention to provide a package of sterile surgical gloves.

It is another object of this invention to provide a package of sterile surgical gloves from which said gloves are readily dispensed under sterile conditions.

It is a further object of the present invention to provide a package of the aforesaid nature resistant to contamination during storage and handling, and amenable to low cost manufacture.

These objects and other objects and advantages of the invention will be apparent from the following description.

SUMMARY OF THE INVENTION

The above and other beneficial objects and advantages are accomplished in accordance with the present invention by a packaged multitude of gloves comprising:

(a) a roll comprised of a continuous spirally wound impervious backing sheet of constant width defined by opposed edges, and having uniformly spaced parallel transverse tear lines, said edges and tear lines defining sequentially disposed contiguous rectangular storage areas, (b) a flattened sterile surgical glove having finger and cuff portions releasibly attached to the backing sheet within each storage area, the glove being oriented such that, when the roll axis is horizontally positioned, and the backing sheet is downwardly unwound, the cuff portion is upwardly directed, and (c) projecting means associated with each cuff portion, causing said cuff portion to automatically open from the flattened state as the roll is unwound, thereby permitting insertion of a hand downwardly into said glove.

In preferred embodiments, the gloves are adhesively attached to the backing sheet, the strength of such attachment being adequate to hold the glove in place during insertion of the hand therein, yet not so strong as to damage the glove or thwart its detachment from the backing sheet. A brake mechanism is preferably associated with the roll to prevent unwinding during insertion of a hand into the glove. The tear lines are such as to enable removal of portions of the backing sheet following removal of gloves from storage areas.

The projecting means may be a weight incorporated into the cuff, or a pleated structure under resilient compression while in the flattened, stored state within the roll. The gloves may be disposed in identical orientation upon the backing sheet, or may be disposed in alternating left and right hand configurations.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 2 is a fragmentary plan view showing gloves as they are dispensed from said roll.

FIG. 3 is a sectional view taken upon the line 3—3 of FIG. 2.

DESCRIPTION OF THE PREFERRED EMBODIMENT

Figure 1:
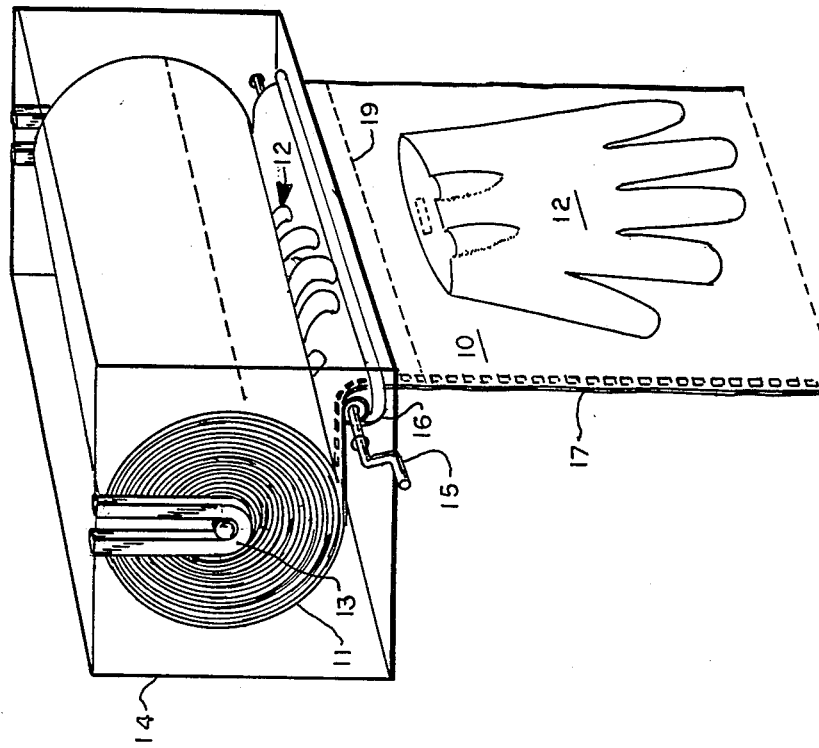
FIG. 1 is a perspective view of an embodiment of a roll package of the present invention shown mounted in a holder facilitating removal of gloves from the package.

Referring to FIGS. 1-3, an embodiment of the package of the present invention is shown comprised of backing sheet 10 wound in the form of spiral roll 11 and having gloves 12 disposed thereupon.

The roll 11 is formed about a central core 13, and the roll is rotatively positioned by means of said core within a horizontally disposed protective enclosure 14 equipped with an advancing crank 15. A toothed sprocket wheel 16 associated with crank 15 engages a series of perforations 17 in backing sheet 10. Advancing crank 15 additionally serves as a brake means which prevents uncontrolled unwinding of the backing sheet from its roll state.

Backing sheet 10 is preferably fabricated of an impervious material such as a film or coated paper, and is of a constant width defined by the distance between opposed edges 18. Uniformly spaced parallel tear lines 19 are disposed transversely to edges 18, and may be comprised of a line of perforations or slits. Edges 18 and tear lines 19 together defined sequentially disposed contiguous rectangular storage areas 20.

The gloves are preferably comprised of a very thin film of an elastomeric material. Talcum powder may be disposed within the glove to permit insertion of a hand therein. The glove is comprised of finger and cuff portions 21 and 22, respectively, and palm and back sides 23 and 24 respectively. One glove is releasably attached within each storage area 20. Attachment may be by means of adhesive 25 disposed upon either the palm or back portion, said attachment being such as to cause the glove to reside in flattened form within the storage area. Other attachment means may, however, be employed.

The glove is oriented such that, when the roll axis is horizontally disposed, and the backing sheet downwardly unwound, cuff portion 22 is upwardly directed. Projecting means, in the form of paired pleats 26, are associated with the palm side of cuff portion 22. Other projecting means may, however, be utilized. The function of the projecting means is to cause the palm side of the glove to automatically move away from the backing sheet, thereby opening the cuff portion so as to receive the hand of the user.

Figure 4:
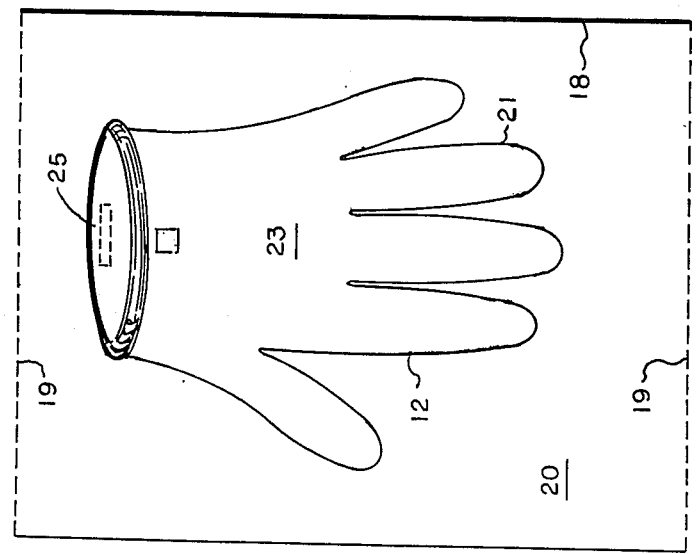
FIG. 4 is a fragmentary plan view of an alternative embodiment of the present invention.

In the embodiment of FIG. 4, the cuff portion has a partially rolled down configuration 28, and the projecting means is in the form of a small weight 29.

In still other embodiments, non-sterile type gloves may be stored and dispensed by way of the aforesaid principles of the present invention.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A package of a multitude of gloves comprising:
   (a) a roll comprised of a continuous spirally wound impervious backing sheet of constant width defined by opposed edges, and having uniformly spaced parallel transverse tear lines, said edges and tear lines defining sequentially disposed contiguous rectangular storage areas,
   (b) a flattened sterile surgical glove having finger and cuff portions releasably attached to the backing sheet within each storage area, the glove being oriented such that, when the roll axis is horizontally positioned, and the backing sheet is downwardly unwound, the cuff portion is upwardly directed, and
   (c) projecting means associated with each cuff portion, causing said cuff portion to automatically open from the flattened state as the roll is unwound, thereby permitting insertion of a hand downwardly into said glove.

2. The package of claim 1 wherein said gloves are adhesively attached to the backing sheet, the strength of such attachment being adequate to hold the glove in place during insertion of a hand therein, yet not so strong as to damage the glove or thwart its detachment from the backing sheet.

3. The package of claim 1 wherein a brake mechanism is associated with the roll to prevent unwinding during insertion of a hand into a glove.

4. The package of claim 3 wherein said tear lines enable removal of portions of the backing sheet following removal of gloves.

5. The package of claim 1 wherein said projecting means is a pleated structure under resilient compression while in the flattened, stored state within the roll.

6. The package of claim 1 wherein said projecting means is a weight incorporated into said cuff portion.

7. The package of claim 1 wherein said gloves are disposed in alternating left and right hand configurations.

8. The package of claim 1 wherein said gloves are comprised of a thin film of elastomeric material and contain talcum powder to facilitate insertion of a hand into the glove.

* * * * *